United States Patent [19]

Takata et al.

[11] Patent Number: 5,182,105
[45] Date of Patent: Jan. 26, 1993

[54] BATHING COMPOSITION

[75] Inventors: Noboru Takata; Junko Arai; Hidenori Yorozu, all of Tochigi, Japan

[73] Assignee: Kao Corporation, Tokyo, Japan

[21] Appl. No.: 754,260

[22] Filed: Aug. 27, 1991

Related U.S. Application Data

[63] Continuation of Ser. No. 426,257, Oct. 25, 1989, abandoned.

[30] Foreign Application Priority Data

Oct. 25, 1988 [JP] Japan ................. 63-268889

[51] Int. Cl.$^5$ .............................................. A61K 31/74
[52] U.S. Cl. .................................. 424/78.02; 424/70; 424/47
[58] Field of Search ................. 424/78, 70, 47, 78.02

[56] References Cited

U.S. PATENT DOCUMENTS 4,529,605  1/1983  Lynch et al. ................. 514/552
4,931,271  6/1990  Lang ................................ 424/47

FOREIGN PATENT DOCUMENTS 0023750 12/1986 European Pat. Off. .

OTHER PUBLICATIONS

Chemical Abstracts, vol. 101, No. 2, Jul. 1984, p. 238, Abstract No. 12002U, Columbus, Ohio, US; E. D. Goddard et al., "Skin Protection by Cationic Cellulose Derivatives in Vitro Test Methods: and Parfuem. Kosmet." 1984, 65(2), 59-67.

*Primary Examiner*—Thurman K. Page
*Assistant Examiner*—D. Gabrielle Phelan
*Attorney, Agent, or Firm*—Sughrue, Mion, Zinn, Macpeak & Seas

[57] ABSTRACT

A bathing composition comprising (1) oily component, (2) nonionic surfactant, and (3) cationic polymer is disclosed. The bathing composition of the present invention makes it possible to render the skin moist after bathing, imparts a smooth feel to the skin during and after bathing, and provide a sustained moistening effect after bathing.

9 Claims, No Drawings

BATHING COMPOSITION

This is a continuation of application Ser. No. 07/426,257, filed Oct. 25, 1989, now abandoned.

FIELD OF THE INVENTION

This invention relates to a bathing composition. More particularly, it relates to a bathing composition which renders the skin moist after bathing, imparts a smooth feel to the skin during and after bathing, and provides a sustained high moistening effect after bathing.

BACKGROUND OF THE INVENTION

Bathing, which has various effects, for example, making our bodies clean, warming not only the limbs but also the whole body to the bones, and physically and mentally relaxing us, is essential to our daily lives.

On the other hand, it is frequently observed that bathing removes oily components from one's skin and thus impart a dryness to the skin after bathing, particularly in winter. In order to suppress the dryness, therefore, it has been attempted to apply, for example, a lotion or a cream to the skin after bathing. However the application of a lotion or a cream requires some time and care in the application. Further, it is difficult for, in particular, aged people to apply these cosmetics over the whole body.

In order to overcome these problems, there have been developed bathing compositions containing oily component(s) and humectant(s). The use of such bathing compositions enables us to care for the skin over the whole body during bathing and thus makes it unnecessary to apply a lotion or a cream after bathing.

Oily components such as oils are effective in suppressing the dryness of the skin after bathing. An example of bathing compositions containing oily components is a so-called oil-bath, wherein oily components float on the bath water. When the employed bathing composition contains a sufficient amount of oily components for suppressing the dryness of the skin, however, these oily components adhere to the skin and impart a sticky feel. In addition, such bathing composition tends to stain the bathtub. Furthermore, the floating oily components offend the eyes.

In order to overcome these problems, a bathing composition wherein oily components are self-emulsified has been proposed (see, e.g., JP-A-61-176520 and JP-A-61-227519 (the term "JP-A" as used herein means an "unexamined published Japanese Patent Application")).

However bathing compositions wherein oily components are emulsified as above are still unsatisfactory from the viewpoints of the moist feel of the skin after bathing and the smooth feel thereof during and after bathing. Furthermore, a sufficient moistening effect cannot be achieved thereby.

SUMMARY OF THE INVENTION

Accordingly, it is an object of the present invention to provide a bathing composition which moistens the skin after bathing, imparts a smooth feel during and after bathing, and provides a sustained high moistening effect after bathing.

In order to achieve this object, we have conducted extensive studies. As a result, we have found that a bathing composition having excellent effects can be obtained by blending an oily component with a non-ionic surfactant together with a cationic polymer whereby the oily component is present in the form of emulsified particles in bath water.

Thus the present invention, which has been completed based on the above finding, provides a bathing composition comprising (1) oily component, (2) non-ionic surfactant, and (3) cationic polymer.

DETAILED DESCRIPTION OF THE INVENTION

The bathing composition of the present invention is described in further detail below.

It is preferable that the oily components to be used in the present invention are insoluble or slightly soluble in water and in the form of a liquid or a solid at room temperature. Examples thereof are as follows.

(1) Fats and oils

Natural fats and oils such as soybean oil, rice bran oil, jojoba oil, avocado oil, almond oil, olive oil, cacao fat, sesame oil, persic oil, castor oil, coconut oil, mink oil, beef tallow and lard; hardened oils obtained by hydrogenating oils as above; and synthetic triglycerides and diglycerides such as myristic acid glyceride, 2-ethylhexanoic acid glyceride, etc.

(2) Waxes

Carnauba wax, spermaceti, beeswax, lanolin, etc.

(3) Hydrocarbons

Liquid paraffin, vaseline, paraffin, microcrystalline wax, ceresin, squalane, pristan, etc.

(4) Higher fatty acids

Lauric acid, myristic acid, palmitic acid, stearic acid, behenic acid, oleic acid, linolic acid, linolenic acid, lanolic acid, isostearic acid, etc.

(5) Higher alcohols

Lauryl alcohol, cetyl alcohol, stearyl alcohol, oleyl alcohol, cholesterol, 2-hexyldecanol, etc.

(6) Esters

Cetyl octanoate, myristyl lactate, cetyl lactate, isopropyl myristate, myristyl myristate, isopropyl palmitate, isopropyl adipate, butyl stearate, decyl oleate, cholesterol isostearate, etc.

(7) Essential oils

Mentha oil, jasmine oil, camphor oil, white cedar oil, bitter orange peel oil, ryu oil, turpentine oil, cinnamon oil, bergamot oil, citrus unshiu orange oil, calamus oil, pine oil, lavender oil, bay oil, clove oil, hiba oil, eucalyptus oil, lemon oil, thyme oil, peppermint oil, rose oil, sage oil, menthol, cineole, eugenol, citral, citronellal, borneol, linalool, geraniol, camphor, thymol, spirantol, pinene, limonene, terpenoid compounds, etc.

(8) Silicone oils

Dimethicone, phenyl dimethicone, dimethicone copolyol, cyclomethicone, etc.

Among these oily components, jojoba oil, olive oil, 2-ethyl hexanoic acid glyceride, squalane, cetyl octanoate and silicone oils are preferred.

Either one of these materials or a mixture thereof may be used in the present invention. The content of the oily component (total content in the case of multiple oily components) in the bathing composition of the present invention may be preferably selected in such a manner as to control the concentration of the oily component in bath water to a range of from 2 to 500 ppm, and more preferably from 10 to 100 ppm. When the concentration of oily component in bath water is less than 2 ppm, improvement in the smoothness of the skin is undesirably lowered. It is generally preferable that the content of oily component ranges from 0.5 to 50 parts by weight, and more preferably from 1 to 30 parts by weight, per 100 parts by weight of the bathing composition.

Examples of the nonionic surfactants to be used in the bathing composition of the present invention include glycerol fatty acid esters, propylene glycol fatty acid esters, sorbitan fatty acid esters, polyoxyethylene sorbitan fatty acid esters, tetraoleic acid polyoxyethylene sorbitol, polyoxyethylene alkyl ethers, polyoxyethylene polyoxypropylene glycol, polyoxyethylene polyoxypropylene alkyl ethers, polyethylene glycol fatty acid esters, polyoxyethylene castor oil, polyoxyethylene hardened castor oil and polyglycerol fatty acid esters. Among these nonionic surfactants, sorbitan fatty acid esters and polyoxyethylene alkyl ethers are preferred.

These nonionic surfactants serve as emulsifiers for the above-mentioned oily components.

Either one of these nonionic surfactants or a mixture thereof may be used in the present invention. It is preferable that the content of nonionic surfactant (total content in the case of multiple nonionic surfactants) ranges from 5 to 100 parts by weight, and more preferably from 18 to 60 parts by weight, per 100 parts by weight of the oily component. When the content of nonionic surfactant is less than 5 parts by weight per 100 parts by weight of the oily component, self-emulsification of the oily component is not sufficiently achieved. When it exceeds 100 parts by weight, on the other hand, preference of the product might be lowered because foaming of bath water tends to increase.

It is preferable that the cationic polymers to be used in the bathing composition of the present invention are soluble in water. Examples thereof include cationic cellulose, cationic dextran, cationic dextrin, chitosan, cationic vinylpyrrolidone polymer, N,N-dimethyl-3,5-methylenepiperidinium chloride polymer and distearyldimethylammoniun chloride polymer.

Among these cationic polymers, cationic cellulose, cationic dextrin, chitosan and distearyldimethylammonium chloride polymer are preferred.

Either one of these cationic polymers or a mixture thereof may be used in the present invention. The content of cationic polymer may be preferably selected in such a manner that the concentration of the cationic polymer in bath water ranges from 0.05 to 100 ppm, and more preferably from 0.1 to 25 ppm. It is generally preferable that the content of cationic polymer (total content in the case of multiple cationic polymers) ranges from 0.01 to 20 parts by weight, and more preferably from 0.05 to 10 parts by weight, per 100 parts by weight of the bathing composition. When the content of cationic polymer is less than 0.01 parts by weight per 100 parts by weight of the bathing composition, the effect of improving the texture of the skin might be lowered. Furthermore, it preferably ranges from 0.1 to 300 parts by weight, and more preferably 0.5 to 150 parts by weight, per 100 parts by weight of the above-mentioned oily component.

Known examples for the application of a cationic polymer to a bathing composition include the use of cationic cellulose (see e.g., WPI Acc No. 84-189961/31; Henckel, West Germany) as well as the use of chitosan and a denatured product thereof (see JP-A-63-10715). The cationic cellulose is used in order to soften the skin and protect the skin from oily soils, while the optionally denatured chitosan is used in order to impart a smooth and moist feel to the skin. However, none of these cationic polymers can satisfactorily suppress the dryness of the skin after bathing.

On the other hand, when the bathing composition of the present invention is introduced into bath water, the oily component forms an emulsion together with the nonionic surfactant(s). Then this emulsion and the cationic polymer exert a synergistic effect of improving the texture of the skin and suppressing the dryness of the skin after bathing.

When cationic polymer is substituted with a cationic surfactant, which is also a cationic substance, the synergistic effect, together with the emulsion, of improving the skin texture, can not be achieved.

In addition to the essential components specified above, the bathing composition of the present invention may further contain various known bathing materials commonly used in bathing preparations. Non-limited examples of the bathing materials are as follows.

(i) Inorganic salts

Sodium chloride, sodium hydrogencarbonate, sodium carbonate, sodium borate, sodium sulfate, sodium sulfide, sodium sesquicarbonate, sodium nitrate, sodium thiosulfate, sodium polyphosphate, sodium phosphate, calcium oxide, magnesium oxide, calcium carbonate, magnesium carbonate, potassium chloride, potassium sulfate, etc.

(ii) Inorganic acids

Boric acid, methasilicic acid, silicin anhydride, etc.

(iii) Organic acids

Succinic acid, fumaric acid, malic acid, tartaric acid, citric acid, benzoic acid, etc.

(iv) Crude drugs

Fennel, phellodendron bark, matricaria, cinnamon bark, safflower, paeoniae radix, ginger, calamus, cnidium rhizome, angericae radix, aurantii nobilis pericarpium, atractylodes lancea rhizoma, Japanese valerian rhizome, angelicae dahuricae radix, bitter orange peel, mentha herb, hoelen, gingseng, etc.

(v) Dyes

The dyes specified in Attached Tables 1 and II of Tar Dyes as provided by a Ministerial Ordinance of The Ministry of Health and Welfare such as yellow dye No. 4, blue dye No. 1 and yellow dye No. 202 and natural dyes authorized as food additives such as chlorophyll, riboflavin, crocin, safflower, anthraquinone, etc.

(vi) Vitamins

Vitamins A, C, D, E, etc.

(vii) Perfumes

(viii) Micropowders

Polymers which are generally called "cosmetic powders" such as acrylic resins, styrene resins, epoxy resins, nylon, polyethylene, polypropylene, polyvinyl chloride, polyethylene terephthalate resins and polytetrafluoroethane, copolymers thereof, silicic acid, calcium silicate, natural aluminum silicate, synthetic aluminum silicate, zeolite, titanium oxide, talc, kaoline, mica, bentonite, etc.

(ix) Others

Sulfur, hot spring deposit, fine sand, mica, neutral clay, roasted rice bran, bactericides, preservatives and materials required for the preparation of the desired bathing composition.

It is preferable that these bathing materials is used in an amount of 0 to 5000 parts by weight per 100 parts by weight of the essential components of the bathing composition of the present invention.

Similar to known bathing preparations, the bathing composition of the present invention may be formulated into various forms such as a powder, granules, tablets or a solution. The methods for formulating the bathing composition of the present invention into such forms are described, for example, in Tadashi Ichibangase ed., *Seizaigaku (Pharmaceutics)*, published by Hirokawasyoten, February 1977.

To further illustrate the effects of the present invention, Examples, Comparative Examples, and Test Evaluation are described below.

EXAMPLES 1 and 2 and COMPARATIVE EXAMPLES 1 to 12

A bathing preparation of each composition as specified in Table 1 was prepared.

EXAMPLES 3 to 13 and COMPARATIVE EXAMPLES 13 to 15

A bathing preparation of each composition as specified in Table 3 was prepared into a form of tablet, except for Example 13, by the following manner. Namely, oily component and dextrin were previously mixed, and the other components as specified in Table 3 were mixed thereto to obtain a powder mixture. Then, 50 g of the resulting powder mixture filled into a metal mold having inner diameter of 50 ϕ, and punched out under the pressure of 200 kg/cm$^2$ to obtain a tablet.

Each bathing composition of the above Examples and Comparative Examples was in the form shown in Tables 1 and 3. Tables 1 and 3 further show the single dose (g) of each product.

Test Evaluation 1

The synergistic effects on the smoothness of the skin, achieved by the combined use of the oily components, which had been emulsified by the nonionic surfactants, with the cation polymers in the bathing composition of the present invention was evaluated in the following manner. Namely, the following tests (1) and (2) were conducted, to thereby evaluate the degrees of the improvement in the smoothness of the skin achieved by ionic materials selected from among anionic, cationic and amphoteric substances and cationic polymers with and without emulsified oily components by using the bathing compositions prepared in Examples 1 and 2 and Comparative Examples 1 to 12.

(1) Two bathtubs each containing 150 l of bathing water at 40° C. were prepared. Nothing was added to the bathing water in one bathtub while a bathing composition of Comparative Example 2 exclusively comprising an ionic substance was added to the other one in an amount specified in Table 1. Right and left forearms of six subjects were immersed in these bathing waters, respectively, and the degrees of the improvement in the smoothness of the skin achieved with and without the use of the ionic substances were evaluated. The average was referred to as the degree of the improvement in the smoothness (a) of the corresponding ionic substance.

Further, the bathing compositions of Comparative Examples 4, 6, 8, 10 and 11, each exclusively comprising an ionic substance, were examined in the same manner, so as to determine the improvement in the smoothness (a) of each ionic substance.

| Improvement in smoothness | Evaluation |
|---|---|
| Not improved | 0 |
| Slightly improved | 1 |
| Improved | 2 |
| Remarkably improved | 3 |

(2) The same bathtubs as those used in the above test (1) were prepared. The bathing composition of Comparative Example 1 free from any ionic substances was dissolved in the bathing water in one bathtub in the amount specified in Table 1, while the bathing composition of Example 1 containing the emulsified oily components and the cationic polymer was dissolved in other one in the amount specified in Table 1. Then right and left forearms of six subjects were immersed in these bathing waters, respectively. Thus the degrees of the improvement in the smoothness of the ionic substances in the presence of the emulsified oily components (b) were evaluated in the same manner as the one described in (1).

Furthermore, the bathing compositions of Comparative Examples 3, 5, 7 and 9, each containing the emulsified oily components and ionic substance, were tested in the same manner so as to evaluate the degrees of the improvement in the smoothness of the skin (b).

The synergistic effect on the smoothness of the skin achieved by emulsified oily components and an ionic substance can be evaluated whether the difference of (b)–(a) is positive or negative. Namely, this difference indicates the improvement in the smoothness obtained by using the ionic substance with or without the use of the emulsified oily components. When this value is positive, the synergistic effect is achieved.

Table 2 shows the results of the above tests (1) and (2).

Test Evaluation 2

In order to examine the effect of the cationic polymer(s) in bathing composition of the present invention, the bathing compositions of Example 4 and Comparative Example 14 were tested in the following manner. Namely, 50 subjects used each bathing composition in a conventional manner for 10 days and the smoothness of the skin of each subject during bathing and the smoothness and moistness thereof after bathing were evaluated. Table 4-1 shows the results.

Further, in order to examine the effect depending upon the amount of the cationic polymer in bathing composition of the present invention, the bathing composition of Example 4 and Comparative Example 15 were tested in the same manner. Table 4-2 shows the results.

Test Evaluation 3

The sustained moistening effect after bathing obtained by the bathing composition of Example 10 was evaluated in the following manner.

A tablet (50 g) of the bathing composition of the Example 10 was dissolved in 150 l of bathing water at 40° C. contained in a bathtub and a subject took a bath therein for 10 minutes followed by immediately towel-drying. Then the skin conductance value at the forearm was determined before bathing and 10, 20, 30 and 60 minutes after bathing by using a high-frequency impedance meter (Model IB-400; manufactured by IBS). The obtained data were compared with control examples which had been obtained by using a bathing water containing no additive. The skin conductance before bathing was designated to as 100, and the test data are expressed as the relative value of each average value. Increase of the skin conductance value means increase of the water content in the horny layer of the skin. Details of methods for determination of the skin conductance and evaluation for the results are described, for example, in Hachiro Tagami, *The journal of Investigative Dermatology*, vol 75, No. 6, pp 500 to 507, 1980, etc. Table 5 shows the results.

Test Evaluation 4

The amounts of oily component of the bathing compositions of Examples 3, 6 and 7 and Comparative Example 13 adhering to the skin were determined in the following manner.

Both forearms of eight subjects were each provided with four bottom-less cups (bottom area: approximately 5 cm$^2$). 5 ml portions of a bathing water, in which the bathing composition of Example 3 had been dissolved at a ratio of one tablet (90 g) per 150 l of water at 40° C., were introduced into the cups on one forearm of each subject, while 5 ml portions of another bathing water, in which the bathing composition of Comparative Example 13 had been dissolved at a ratio of a tablet (90 g) per 150 l, were introduced into the cups on another forearm. After allowing to stand for 10 minutes, these solutions and cups were removed and the skin of each subject was lightly rinsed with distilled water and dried.

Next, bottom-less cups were located on the same positions and a mixture of acetone and ether (1:1 by volume) was introduced into each cup. After allowing to stand for 10 minutes, oily component that had been absorbed by the skin was extracted. The acetone/ether mixture contained in four cups in each lot were recovered and evaporated to dryness, to thereby give a sample. These samples were subjected to capillary gas chromatography so as to determine the oily component (cetyl octanoate) that had been adsorbed by the skin. Table 6 shows the results.

TABLE 1

|  | Example 1 | Example 2 | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 | Comp. Ex. 10 | Comp. Ex. 11 | Comp. Ex. 12 |
|---|---|---|---|---|---|---|---|---|---|---|---|---|---|---|
| Oily component | | | | | | | | | | | | | | |
| Liquid paraffin | 10 | 10 | 10 | | 10 | | 10 | | 10 | | 10 | | | 0.1 |
| Cholesteryl isostearate | 1 | 1 | 1 | | 1 | | 1 | | 1 | | 1 | | | 0.01 |
| Nonionic Surfactant | | | | | | | | | | | | | | |
| Polyoxyethylene oleyl ether (2 E.O.) | 1.2 | 1.2 | 1.2 | | 1.2 | | 1.2 | | 1.2 | | 1.2 | | | 0.012 |
| Polyoxyethylene oleyl ether (10 E.O.) | 0.8 | 0.8 | 0.8 | | 0.8 | | 0.8 | | 0.8 | | 0.8 | | | 0.008 |
| Anionic Substance | | | | | | | | | | | | | | |
| Polyoxyethylene Lauryl ether sodium sulfate (3 E.O.) | | | | 0.15 | 0.15 | | | | | | | | | |
| Cationic Substance | | | | | | | | | | | | | | |
| Benzalkonium chloride | | | | | | 0.15 | 0.15 | | | | | | | |
| Distearyldimethyl-ammonium chloride | | | | | | | | 0.15 | 0.15 | | | | | |
| Amphoteric Substance | | | | | | | | | | | | | | |
| Betaine cetyldi-methylaminoacetate | | | | | | | | | | 0.15 | 0.15 | | | |
| Cationic Polymer | | | | | | | | | | | | | | |
| Cationic cellulose | 0.15 | | | | | | | | | | | 0.15 | | 0.15 |
| Cationic dextran | | 0.15 | | | | | | | | | | | 0.15 | |
| Form of Bathing Composition | Liquid | Liquid | Liquid | Liquid | Liquid | Powder | Liquid | Paste | Liquid | Liquid | Liquid | Powder | Powder | Powder |
| Single Dose (g/150 l of water) | 13.15 | 13.15 | 13.0 | 0.15 | 13.15 | 0.15 | 13.15 | 0.15 | 13.15 | 0.15 | 13.15 | 0.15 | 0.15 | 0.28 |

Note: All values other than single doses are parts by weight

TABLE 2

| Components of the Bathing Composition | Comparative Example 2 | Comparative Example 3 | Comparative Example 4 | Comparative Example 5 | Comparative Example 6 | Comparative Example 7 | Comparative Example 8 | Comparative Example 9 |
|---|---|---|---|---|---|---|---|---|
| Ionic substance | Anionic Substance | | Cationic Substance | | | | Amphoteric Substance | |
| Oily components and Nonionic surfactants | None | Present | None | Present | None | Present | None | Present |
| Improvement in | 0 | 0 | 0.5 | 0.5 | 0.7 | 0.2 | 1.3 | 0.5 |

TABLE 2-continued

| Smoothness | (a) | (b) | (a) | (b) | (a) | (b) | (a) | (b) |
|---|---|---|---|---|---|---|---|---|
| (b) − (a) | 0 | | 0 | | 0.5 | | −0.8 | |

| Components the Bathing Composition | Comparative Example 10 | Example 1 | Comparative Example 11 | Example 2 | Comparative Example 12 | Example 1 |
|---|---|---|---|---|---|---|
| Ionic substance | | | Cationic Polymer | | | |
| Oily components and Nonionic surfactants | None | Present | None | Present | Present | Present |
| Improvement in Smoothness | 1.3 (a) | 2.3 (b) | 1.0 (a) | 2.2 (b) | 1.4 (a) | 2.3 (b) |
| (b) − (a) | +1.0 | | +1.2 | | +0.9 | |

TABLE 3

| | Example | | | | | | | | | | | Comparative Example | | |
|---|---|---|---|---|---|---|---|---|---|---|---|---|---|---|
| | 3 | 4 | 5 | 6 | 7 | 8 | 9 | 10 | 11 | 12 | 13 | 13 | 14 | 15 |
| Oily component | | | | | | | | | | | | | | |
| Cetyl octanoate | 11.4 | 5.4 | 5.4 | 5.4 | 5.4 | 5.4 | 5.4 | 5.4 | 5.4 | | 34 | 11.4 | 5.4 | 5.4 |
| Cholesteryl isostearate | | 0.4 | 0.4 | 0.4 | 0.4 | 0.4 | 0.4 | 0.4 | 0.4 | 1 | | | 0.4 | 0.4 |
| White vaseline | | 0.8 | 0.8 | 0.8 | 0.8 | 0.8 | 0.8 | 0.8 | 0.8 | | 4 | | 0.8 | 0.8 |
| Myristic acid isostearic acid diglyceride | | 0.4 | 0.4 | 0.4 | 0.4 | 0.4 | 0.4 | 0.4 | 0.4 | | | | 0.4 | 0.4 |
| Liquid paraffin | | | | | | | | | | 9 | | | | |
| Nonionic Surfactant | | | | | | | | | | | | | | |
| Polyoxyethylene stearyl ether (6 E.O.) | 0.9 | 1.2 | 1.2 | 1.2 | 1.2 | 1.2 | 1.2 | 1.2 | 1.2 | | 3.2 | 0.9 | 1.2 | 1.2 |
| Polyoxyethylene oleyl ether (9 E.O.) | 2 | 0.8 | 0.8 | 0.8 | 0.8 | 0.8 | 0.8 | 0.8 | 0.8 | | 2.1 | 2 | 0.8 | 0.8 |
| Polyoxyethylene oleyl ether (2 E.O.) | | | | | | | | | 1.2 | | | | | |
| Polyoxyethylene oleyl ether (10 E.O.) | | | | | | | | | | 0.8 | | | | |
| Cationic Polymer | | | | | | | | | | | | | | |
| Cationic cellulose | 0.15 | 0.15 | | | | | | 0.07 | 0.07 | 0.15 | 1 | | | 0.005 |
| Cationic dextran | | | 0.15 | | | | | | | | | | | |
| Cationic dextrin | | | | 0.15 | | | | | | | | | | |
| Cationic vinyl pyrrolidone polymer | | | | | 0.15 | | | | | | | | | |
| Chitosan | | | | | | 0.15 | | | | | | | | |
| N,N-dimethyl-3,5-methylenepiperidinium chloride polymer | | | | | | | 0.15 | | | | | | | |
| Other Bathing Material | | | | | | | | | | | | | | |
| Sodium hydrogen-carbonate | 15 | 20 | 20 | 20 | 20 | 20 | 20 | 20 | 20 | 20 | | 15 | 20 | 20 |
| Sodium carbonate | 8 | 10 | 10 | 10 | 10 | 10 | 10 | 10 | 10 | 10 | | 8 | 10 | 10 |
| Succinic acid | 25 | 30 | 30 | 30 | 30 | 30 | 30 | 30 | | 30 | | 23 | 30 | 30 |
| Fumaric acid | | | | | | | | | 30 | | | | | |
| Dextrin | 30 | 30 | 30 | 30 | 30 | 30 | 30 | 30 | 30 | 30 | | 30 | 30 | 30 |
| Perfume | 0.5 | 1 | 1 | 1 | 1 | 1 | 1 | 1 | 1 | 1 | 1 | 0.5 | 1 | 1 |
| Purified water | | | | | | | | | | | 54.7 | | | |
| Form of Bathing Composition | Tablet | Tablet | Tablet | Tablet | Tablet | Tablet | Tablet | Tablet | Tablet | Tablet | Liquid | Tablet | Tablet | Tablet |
| Single Dose (g) | 90 | 50 | 50 | 50 | 50 | 50 | 50 | 50 | 50 | 70 | 20 | 90 | 50 | 50 |

Note: All values other than single doses are parts by weight.

TABLE 4-1

Comparison of products Example 4 and Comparative Example 14

| | Number of subjects | | |
|---|---|---|---|
| Evaluation | Preferring Example 4 | Almost equal | Preferring Comparative Example 14 |
| Smoothness of the skin during bathing | 38 | 10 | 2 |
| Smoothness of the skin after bathing | 28 | 14 | 8 |
| Moistness after bathing | 40 | 7 | 3 |

TABLE 4-2

Comparison of products Example 4 and Comparative Example 15

| Evaluation | Number of subjects | | |
|---|---|---|---|
| | Preferring Example 4 | Almost equal | Preferring Comparative Example 15 |
| Smoothness of the skin during bathing | 42 | 7 | 1 |
| Smoothness of the skin after bathing | 33 | 12 | 5 |
| Moistness after bathing | 45 | 3 | 2 |

TABLE 5

| | Skin conductance value after bathing | | | |
|---|---|---|---|---|
| | After 10 minutes | After 20 minutes | After 30 minutes | After 60 minutes |
| Example 10 | 230 ± 21 | 153 ± 8 | 134 ± 17 | 107 ± 8 |
| Control | 165 ± 18 | 97 ± 8 | 87 ± 8 | 73 ± 6 |

Note: Every value shows mean ± S.E. Referring to skin conductance before bathing as 100.

TABLE 6

| | Cetyl octanoate adsorbed by the skin (g/cm$^2$) |
|---|---|
| Example 3 | 0.53 ± 0.02 |
| Comparative Example 13 | 0.25 ± 0.02 |
| Example 6 | 0.35 ± 0.02 |
| Comparative Example 13 | 0.24 ± 0.04 |
| Example 7 | 0.57 ± 0.06 |
| Comparative Example 13 | 0.25 ± 0.09 |

Note: Every value shows mean ± S.E.

Based on the foregoing testing, it is clear that the bathing composition of the present invention makes it possible to render the skin moist after bathing, impart a smooth feel to the skin during and after bathing and provide a sustained moistening effect after bathing.

While the invention has been described in detail and with reference to specific examples thereof, it will be apparent to one skilled in the art that various changes and modifications can be made therein without departing from the spirit and scope thereof.

What is claimed is:

1. A bathing composition consisting essentially of:
   (1) from 0.5 to 50 parts by weight per 100 parts by weight of the bathing composition of an oily component selected from the group consisting of fats and oils, waxes, hydrocarbons, higher fatty acids, higher alcohols, esters, essential oils and silicone oils,
   (2) from 5 to 100 parts by weight per 100 parts by weight of the oily component (1) of a nonionic surfactant selected from the group consisting of glycerol fatty acid esters, propylene glycol fatty acid esters, sorbitan fatty acid esters, polyoxyethylene sorbitan fatty acid esters, tetraoleic acid polyoxyethylene sorbitol, polyoxyethylene alkyl ethers, polyoxyethylene polyoxypropylene glycol, polyoxyethylene polyoxypropylene alkyl ethers, polyethylene glycol fatty acid esters, polyoxyethylene castor oil, polyoxyethylene hardened castor oil and polyglycerol fatty acid esters, and
   (3) from 0.01 to 20 parts by weight per 100 parts by weight of the bathing composition of a cationic polymer selected from the group consisting of cationic cellulose, cationic dextran, cationic dextrin, chitosan, cationic vinylpyrrolidone polymer, N,N-dimethyl-3,5-methylenepiperidinium chloride polymer and distearyldimethylammonium chloride polymer.

2. The bathing composition as claimed in claim 1, wherein said oily component is self-emulsified with said nonionic surfactant in bath water.

3. The bathing composition as claimed in claim 1, wherein said oily component is insoluble or slightly soluble in water.

4. The bathing composition as claimed in claim 1, wherein the content of said oily component ranges from 1 to 30 parts by weight per 100 parts by weight of the bathing composition.

5. The bathing composition as claimed in claim 1, wherein the content of said nonionic surfactant ranges from 18 to 60 parts by weight per 100 parts by weight of said oily component.

6. The bathing composition as claimed in claim 1, wherein the content of said cationic polymer ranges from 0.05 to 1 parts by weight per 100 parts by weight of the bathing composition.

7. The bathing composition as claimed in claim 1, wherein the content of said cationic polymer ranges form 0.1 to 300 parts by weight per 100 parts by weight of said oily component.

8. The bathing composition as claimed in claim 7, wherein the content of said cationic polymer ranges from 0.5 to 150 parts by weight per 100 parts by weight of said oily component.

9. A bathing composition as in claim 1, wherein the oily component is at least one compound selected from the group consisting of soybean oil, rice bran oil, jojoba oil, avocado oil, almond oil, olive oil, cacao fat, sesame oil, persic oil, castor oil, coconut oil, mink oil, beef tallow and lard, hardened oils obtained by hydrogenation thereof, myristic acid glyceride, 2-ethylhexanoic acid glyceride, carnauba wax, spermaceti, beeswax, lanolin, liquid paraffin, vaseline, paraffin, microcrystalline wax, ceresin, squalane, pristan, lauric acid, myristic acid, palmitic acid, stearic acid, behenic acid, oleic acid, linolic acid, linolenic acid, lanolic acid, isostearic acid, lauryl alcohol, cetyl alcohol, stearyl alcohol, oleyl alcohol, cholesterol, 2-hexyldecanol, cetyl octanoate, myristyl lactate, cetyl lactate, isopropyl myristate, myristyl myristate, isopropyl palmitate, isopropyl adipate, butyl stearate, decyl oleate, cholesterol isostearate, mentha oil, jasmine oil, camphor oil, white cedar oil, bitter orange peel oil, ryu oil, turpentine oil, cinnamon oil, bergamot oil, citrus unshiu orange oil, calamus oil, pine oil, lavender oil, bay oil, clove oil, hiba oil, eucalyptus oil, lemon oil, thyme oil, peppermint oil, rose oil, sage oil, menthol, cineole, eugenol, citral, citronellal, borneol, linalool, geraniol, camphor, thymol, spirantol, pinene, limonene, terpenoid compounds, dimethicone, phenyl dimethicone, dimethicone copolyol and cyclomethicone.

* * * * *